(12) United States Patent
Gopalsami et al.

(10) Patent No.: US 7,223,608 B2
(45) Date of Patent: May 29, 2007

(54) RESONANCE-ENHANCED DIELECTRIC SENSING OF CHEMICAL AND BIOLOGICAL SPECIES

(75) Inventors: Nachappa Gopalsami, Naperville, IL (US); Apostolos C. Raptis, Downers Grove, IL (US)

(73) Assignee: U Chicago Argonne LLC, Chicago, IL (US)

( * ) Notice: Subject to any disclaimer, the term of this patent is extended or adjusted under 35 U.S.C. 154(b) by 205 days.

(21) Appl. No.: 10/637,127

(22) Filed: Aug. 8, 2003

(65) Prior Publication Data

US 2005/0032233 A1 Feb. 10, 2005

(51) Int. Cl.
*G01N 27/00* (2006.01)
(52) U.S. Cl. ............... 436/149; 422/98; 422/82.01
(58) Field of Classification Search ............ 422/98, 422/82.01; 436/149, 150, 151, 153
See application file for complete search history.

(56) References Cited

U.S. PATENT DOCUMENTS

| | | | | |
|---|---|---|---|---|
| 5,382,414 A | * | 1/1995 | Lautenschlager | ........... 422/186 |
| 5,397,993 A | * | 3/1995 | Tews et al. | ................. 324/634 |
| 6,496,018 B1 | * | 12/2002 | Nagata et al. | .............. 324/636 |
| 6,890,715 B1 | * | 5/2005 | Lewis et al. | .................... 435/6 |
| 2002/0005725 A1 | * | 1/2002 | Scott | .......................... 324/637 |
| 2003/0012867 A1 | * | 1/2003 | Madaras et al. | ............... 427/8 |

* cited by examiner

*Primary Examiner*—Jill Warden
*Assistant Examiner*—Natalia Levkovich
(74) *Attorney, Agent, or Firm*—Joan Pennington (57) ABSTRACT

A dielectric sensing method and apparatus are provided for detection and classification of chemical and biological materials. Resonance patterns of a sample within a resonator are detected for identifying a shift in resonance frequency and a change of line width before and after introduction of the sample. The identified shift in resonance frequency and change of line width are used for determining a complex dielectric constant of the sample for the material detection and classification. A degree of selectivity at any excitation frequency is enabled for the dielectric sensing method from the manner in which the complex dielectric constant of a material affects the resonance pattern of the resonator with respect to shift in resonance frequency and the change in line width. By selecting the excitation frequencies to generally correspond to one of the resonance frequencies of the sample material under test, the degree of selectivity and the sensitivity of detection are enhanced.

15 Claims, 6 Drawing Sheets

RESONANCE-ENHANCED DIELECTRIC SENSING OF CHEMICAL AND BIOLOGICAL SPECIES

CONTRACTUAL ORIGIN OF THE INVENTION

The United States Government has rights in this invention pursuant to Contract No. W-31-109-ENG-38 between the United States Government and Argonne National Laboratory.

FIELD OF THE INVENTION

The present invention relates to a novel dielectric sensing method and apparatus for detection and classification of chemical and biological materials.

DESCRIPTION OF THE RELATED ART

A dielectric is a substance or material that has very low electrical conductivity. The dielectric constant of a material is the ratio of the strength of an electric field in a vacuum to that in the dielectric for the same distribution of charge. The dielectric property of a material, whether it is solid, liquid or gas, generally changes with material property, chemical property and excitation frequency. There are many methods for measuring the dielectric properties of materials, such as lumped element, transmission line, free-space, and resonate techniques. These techniques, depending on sample size and geometry can provide accurate determination of complex dielectric constants of materials in a laboratory setting. However, though many methods of measuring the dielectric properties of materials exist in the literature, such methods lack specificity in identifying materials. Few chemical or biological sensors based on such dielectric measurements exist at this time.

A need exist for an effective real-time dielectric sensor for detection and classification of chemical and biological species.

A principal object of the present invention is to provide a dielectric sensing method and apparatus for detection and classification of chemical and biological materials.

SUMMARY OF THE INVENTION

In brief, a dielectric sensing method and apparatus are provided for detection and classification of chemical and biological materials. Resonance patterns of a sample within a resonator are detected for identifying a shift in resonance frequency and a change of line width before and after introduction of the sample. The resonance patterns can be generated either as a function of sample concentration or as a function of excitation frequency for a given sample. The identified shift in resonance frequency and change of line width are used for determining a complex dielectric constant of the sample for the material detection and classification.

In accordance with features of the invention, a degree of selectivity at any excitation frequency is enabled for the dielectric sensing method of the invention from the manner in which the complex dielectric constant of a material affects the resonance pattern of the resonator with respect to shift in resonance frequency and the change in line width. By selecting the excitation frequencies to generally correspond to one of the resonance frequencies of the sample material under test, the degree of selectivity and the sensitivity of detection are enhanced.

In accordance with features of the invention, a cylindrical microwave cavity resonator is used for dielectric sensing and changes in the resonant frequency and quality factor before and after introduction of the sample for small perturbation to the cavity field are identified. The cylindrical microwave cavity resonator is used for gas and solid samples and an RF parallel-plate resonator is used for subsurface liquid contaminant detection.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Features of the preferred embodiment include a new method that provides a degree of selectivity based on the extent to which the complex dielectric constant of a material affects the signal pattern of a resonator. A microwave cavity has been used to demonstrate the proof of principle of selectively detecting gas-phase chemicals and biological macromolecules. The method is applicable at any excitation frequency from RF to terahertz range; however, if the excitation frequency is selected to correspond to one of the resonance frequencies, relaxation-type or spectroscopic, of the material under investigation, the degree of selectivity and the sensitivity of detection can be improved significantly. For example, dielectric materials exhibit relaxation-type resonance at microwave frequencies, and DNA molecules appear to exhibit distinct resonance interactions at terahertz frequencies. With such unique absorption spectra being identified for materials, the method can be applied to a standoff sensing configuration. The resonance-enhanced dielectric method, thus, holds the potential for a fast first screening of chemical or biological agents in the form of gas, powder, or aerosol.

This resonance technique, because of its high quality factor, offers higher detection sensitivities than non-resonant techniques. The method of the invention has a range of applications in including pollutant monitoring, automobile exhaust gas emissions, detection of biowarfare agents in the form of aerosols or powdered spores, chemical warfare agents and long-term monitoring of subsurface contaminant plumes.

The dielectric property of a material is described by its complex dielectric constant, denoted by $\epsilon = \epsilon' - j\epsilon''$. The real part, $\epsilon'$, is known as the permittivity, and the imaginary part, $\epsilon''$, represents the loss in the material. The loss may be due to dielectric damping of the vibrating dipoles and/or due to its conductivity, $\sigma$. The equivalent loss is described by $(\epsilon'' + \sigma/\omega)$, where $\omega$ is the frequency in radians. Dielectric constants of materials are often stated in terms of relative permittivity, $\epsilon_r'$ and the loss tangent, $\tan\delta$, in which $\epsilon_r' = \epsilon'/\epsilon_0$, where $\epsilon_0$ is the permittivity of free space, and $\tan\delta = (\omega\epsilon'' + \sigma)/\omega\epsilon'$.

The dielectric constant of a material generally changes with the excitation frequency, physical property, chemical property, and constituent volume contents. A variation of complex electric susceptibility $\chi_e$ of a typical solid or liquid dielectric material and $\chi_e$ is related to dielectric constant by $\chi_e = 1 + \epsilon_r' - j\epsilon_r''$, which includes dipole ($\chi_{ed}$), ionic ($\chi_{ei}$), and electronic ($\chi_{ee}$) polarizations. In the RF and MW frequency range, the well-known Debye equation gives the variation of $\epsilon_r'$ and $\epsilon_r''$ as a function of frequency:

$$\varepsilon_r'(\omega) = \varepsilon_{r\infty}' + \frac{\varepsilon_{rs}' - \varepsilon_{r\infty}'}{1 + (\omega\tau)^2} \quad (1)$$

$$\varepsilon_r''(\omega) = \left(\frac{\varepsilon_{rs}' - \varepsilon_{r\infty}'}{1 + (\omega\tau)^2}\right)\omega\tau \quad (2)$$

where $\epsilon'_{rs}$ and $\epsilon'_{r\infty}$ are the real part of permittivity at zero and very large frequencies, respectively, and $\tau$ is the relaxation time constant of the material. Near the relaxation frequency of the material, the $\epsilon'$ sharply decreases with frequency and $\epsilon''$ exhibits resonance behavior.

The dielectric constant of gases depends on the polar nature of the molecule, as well as frequency of excitation, pressure, and temperature. The real part, $\epsilon_r'$ is generally related to square of the index of refraction, and the imaginary part, $\epsilon_r''$ is related to spectral absorption of gases corresponding to rotational, vibrational, or electronic energy transitions that occur at microwave, infrared, and optical frequencies, respectively.

Resonant perturbation techniques offer a sensitive means of measuring the dielectric properties of low-loss and medium-loss materials. Resonant perturbation techniques are suitable for gases, solids, or liquids, and allow flexibility in sample size and shape. Commonly used resonant devices include transmission-line resonator in the RF, cylindrical cavity in the microwave, and Fabry-Perot cavity in the millimeter-wave spectral ranges. The complex dielectric constant of a sample placed in a resonator can be deduced from the changes in the resonant frequency and the quality factor before and after introduction of the sample for small perturbation to the cavity field. The underlying perturbation equations are:

$$\frac{f_0 - f_s}{f_s} = (\varepsilon_r' - 1)\frac{C}{2} \quad (3)$$

$$\left[\frac{1}{Q_{Us}} - \frac{1}{Q_{U0}}\right] = \varepsilon_r'' C \quad (4)$$

-continued
with $$C = \frac{\int_{V_s} E_0 E_s dV}{\int_{V_r} |E_0|^2 dV}$$

where $f_0$ and $f_s$ are the resonant frequencies, $Q_{U0}$ and $Q_{Us}$ are the unloaded quality factors, $E_0$ and $E_s$ are the electric field in the cavity, before and after introduction of the sample, respectively, and $V_s$ and $V_r$ are the sample and resonator volumes, and C is assumed to be a constant for small perturbations. In this case, the shift in resonance frequency $\delta F$ denoted by the left hand side of Equation (3) is proportional to the $\epsilon_r'$, and the change in line width $\delta T$ denoted by the left hand side of Equation (4) is proportional to $\epsilon_r''$. The dielectric sensing technique of the preferred embodiment uses these two measurement parameters in the material detection and identification scheme.

Figure 1:
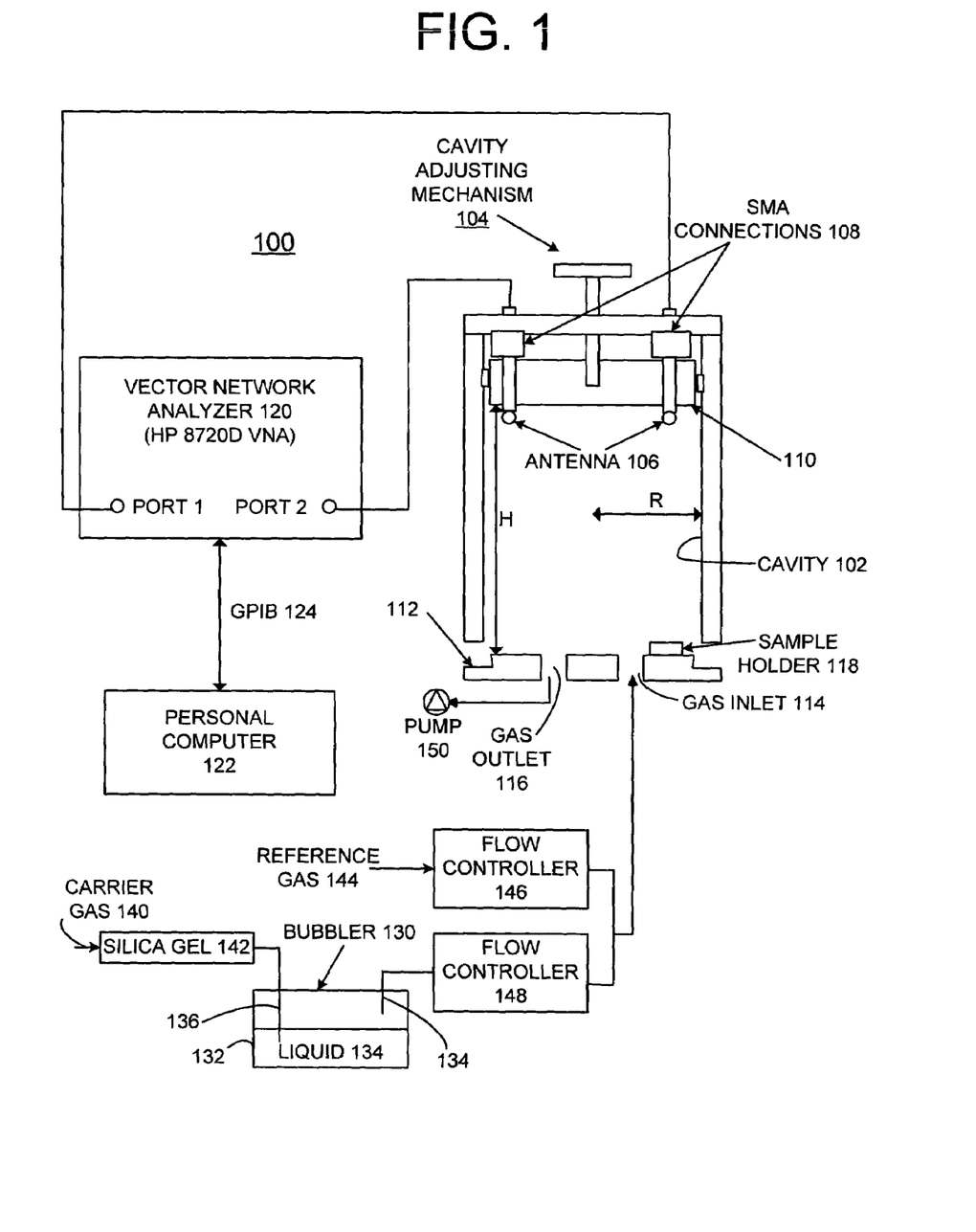
FIG. 1 is a schematic diagram illustrating an exemplary microwave cavity resonator, cavity coupling, tuning mechanism, and the measurement setup for implementing dielectric sensing methods in accordance with the preferred embodiment.

Having reference now to the drawings, in FIG. 1 there is shown an exemplary microwave cavity resonator generally designated by reference character 100 for implementing dielectric sensing methods of the preferred embodiment. Microwave cavity resonator 100 of the preferred embodiment is arranged as $TE_{011}$ mode cylindrical cavity for dielectric testing of gases and solids. A $TE_{011}$-mode cylindrical cavity for dielectric testing was designed and built because of its circular electric field, which allows openings between the cavity wall and the end plates for frequency tuning and sample placement without breaking the electric current circulation.

Microwave cavity resonator 100 of the preferred embodiment includes a cylindrical microwave cavity 102, for example, made of brass with a radius labeled R of 2 cm and a height labeled H adjustable from 1.5 cm to 4 cm by a cavity adjusting screw mechanism generally designated by reference character 104. Cylindrical microwave cavity 102 can support resonance frequencies for the adjustable height of 1.5 cm and 4 cm corresponding to 13.5 GHz to 10 GHz, respectively.

Cylindrical microwave cavity 102 is coupled by a pair of loop antennas 106. Each loop antennas 106 is attached to a respective SMA connector 108 and mounted on an upper cavity plate 110. The coupling strength can be varied by adjusting the relative position of the pair of loop antennas 106 with respect to the cavity face. Cylindrical microwave cavity 102 includes a lower cavity plate 112 having a gas inlet 114 and a gas outlet 116. The positions of the gas inlet 114 and gas outlet 116 do not have much bearing on the measurement sensitivity because the gas samples occupy the whole cavity space 102. Solid samples, however, must be placed at locations of maximum electric or magnetic field for sensitive measurements. A sample holder 118 for solids samples preferably is located on the bottom plate 112 at 0.48×radius where the magnetic field is maximum.

The cavity response is measured by a vector network analyzer (VNA) 120 using the $S_{21}$ transmission mode. Vector network analyzer 120 can be implemented, for example, with a HP 8720D vector network analyzer. Data is collected from the vector network analyzer 120 by a personal computer 122 using GPIB interface 124 and processed in the computer 122 using, for example, LabVIEW application software.

The network analyzer 120, after two-port calibration at the cavity ports with open, short, and load, was set to measure the cavity transmission parameter $S_{21}$ from port 1 to port 2.

Figure 2A:
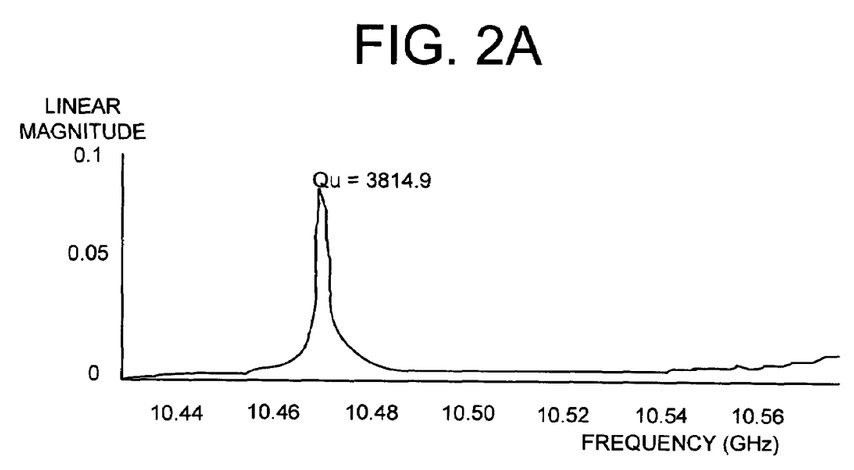
FIGS. 2A and 2B are charts illustrating a typical resonance response of the cavity of FIG. 1.
Figure 2B:
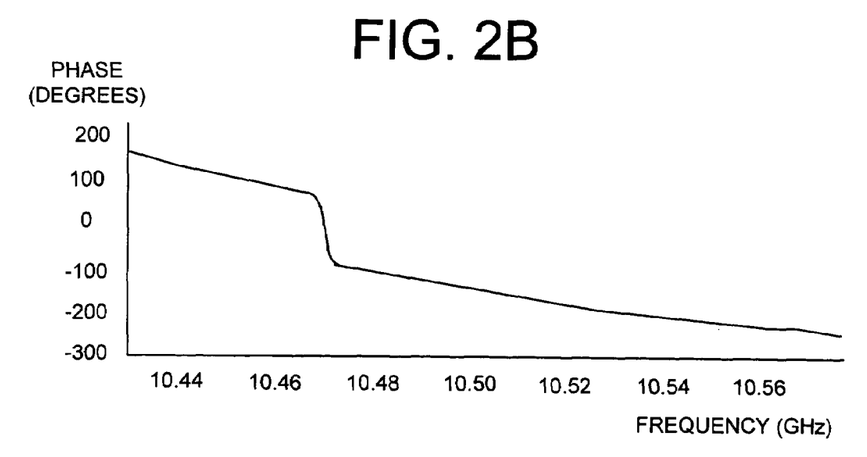
Figure 3:
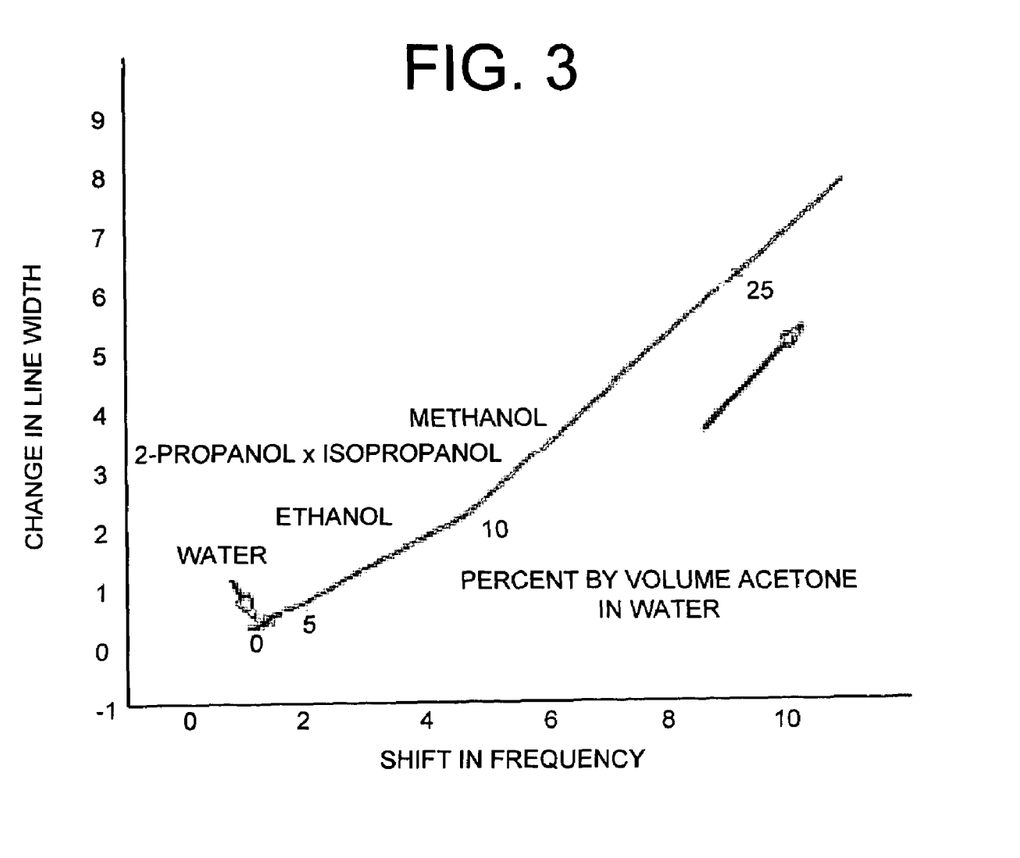
FIG. 3 is a chart illustrating a dielectric signature of a plurality of hydrocarbon gases with change in line width shown relative to a vertical axis and shift in resonance frequency shown relative to a horizontal axis.

Referring to FIGS. 2A, 2B and 3, FIGS. 2A and 2B illustrate a typical resonance response of the cavity 102 obtained over a frequency range of 10.425 to 10.575 GHz. FIG. 3 illustrates a dielectric signature of a plurality of hydrocarbon gases. The loaded quality factor $Q_L$ can be determined from the resonance line, as shown in FIG. 2A, by:

$$Q_L = \frac{f}{\delta f'} \quad (5)$$

where f is the resonance frequency of the resonator and $\delta f$ is the full width at half maximum of the resonance line. The unloaded quality factor, $Q_U$ is then obtained from:

$$Q_U = \frac{Q_L}{1 - |S_{21p}|}, \quad (6)$$

where $Q_U$ is the unloaded quality factor and $|S_{21p}|$ is the peak value of the magnitude of $S_{21}$; the calculated $Q_U$ for the response in FIG. 2A equals 3814.9.

Referring to FIG. 1, the gases under test were derived from liquid samples and admitted into the cavity 102 using a bubbler arrangement generally designated by reference character 130. The bubbler 130 includes a sealed container 132 partially filled with the liquid under test 134 and inserted with a pair tubes 136 and 138, one long tube 136 dipped into the liquid and the other short tube 138 into the headspace of the liquid. A carrier gas 140 connected to the long tube 136 bubbles through the liquid and the entrapped vapor in the bubbles quickly reaches liquid/vapor equilibrium. The air/vapor mixture in the headspace is extracted out from the short tube 138. The vapor concentration at the output of the bubbler 130 depends on the vapor pressure of the liquid 134 and the flow rate of the carrier gas 140. For example, house air, after passing through a silica gel 142, such as Drierite, to remove moisture, was used as the carrier gas 140. A reference gas 144, such as $N_2$, is applied to a flow controller 146 and the test gas from the bubbler 130 is applied to a flow controller 148. The flow rates of reference and test gases were kept constant at 100 cc/m while a small pump 150 evacuated the cavity 102 at a higher flowrate (3 L/min) so that a slight negative pressure was maintained in the cavity 102.

FIG. 3 illustrates results of six chemicals that were tested including water, methanol, ethanol, propanol, 2-propanol, and acetone. FIG. 3 plots the line width change $\delta T$ against the frequency shift $\delta F$ of the six chemicals tested at an arbitrary chosen (empty-cavity) resonance frequency of 10.33 GHz. In the case of acetone, the acetone was diluted with water, and the $\delta T$ values were plotted for concentrations ranging from 0 to 30 percent by volume. Depending on the permittivity and loss factor of the samples, the response pattern shows a degree of selectivity for the chemicals.

The microwave cavity 102 has been used for dielectric testing of biomolecules. The biomolecules were prepared or procured in powder form and were introduced in known quantities into a Teflon sample holder 118 located at 0.48× radius on the bottom plate 112, where the magnetic field is maximum. The bottom plate 112 is mounted on a computer controlled translation stage (not shown) so that the bottom plate can be lowered for sample loading and raised to the same position for closing the cavity.

Four powder samples were tested in the cavity by recording the $S_{21}$ parameters at varying concentrations. The samples tested were acetaminophen (powdered Tylenol caplet), isobutylphenyl propionic acid (powdered Ibuprofen caplet), bovine albumin (protein) from Sigma-Aldrich, and herring sperm DNA from Sigma-Aldrich. The cavity with the Teflon sample holder was tuned to a reference resonance frequency of 10.43 GHz.

Figure 4:
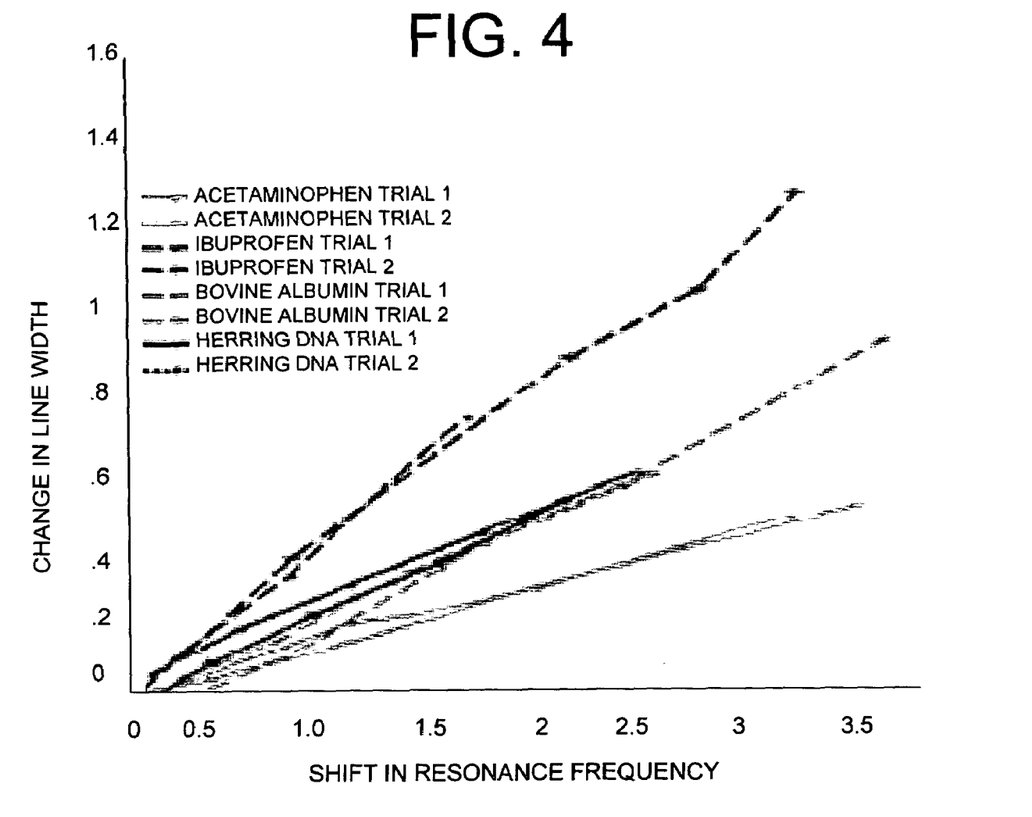
FIG. 4 is a chart illustrating a dielectric signature of a plurality of biological molecules in powder form with change in line width shown relative to a vertical axis and shift in resonance frequency shown relative to a horizontal axis.

In FIG. 4, the $\delta T$-$\delta F$ response patterns of the powder samples are plotted in increments of 0.02 g. The sequence of samples was tested twice, on two different days, for repeatability. The response pattern for each sample was repeatable especially at higher concentrations. Factors that may cause measurement errors at low concentrations include nonuniformity in powder preparation, powder density, powder heaping, and the moisture content. Ibuprofen shows the highest slope in the cavity response and acetaminophen the smallest slope; the bovine albumin and the herring sperm DNA show intermediate slopes. Overall, the results show the effectiveness of the dielectric method for identification of biological macromolecules.

Figure 5:
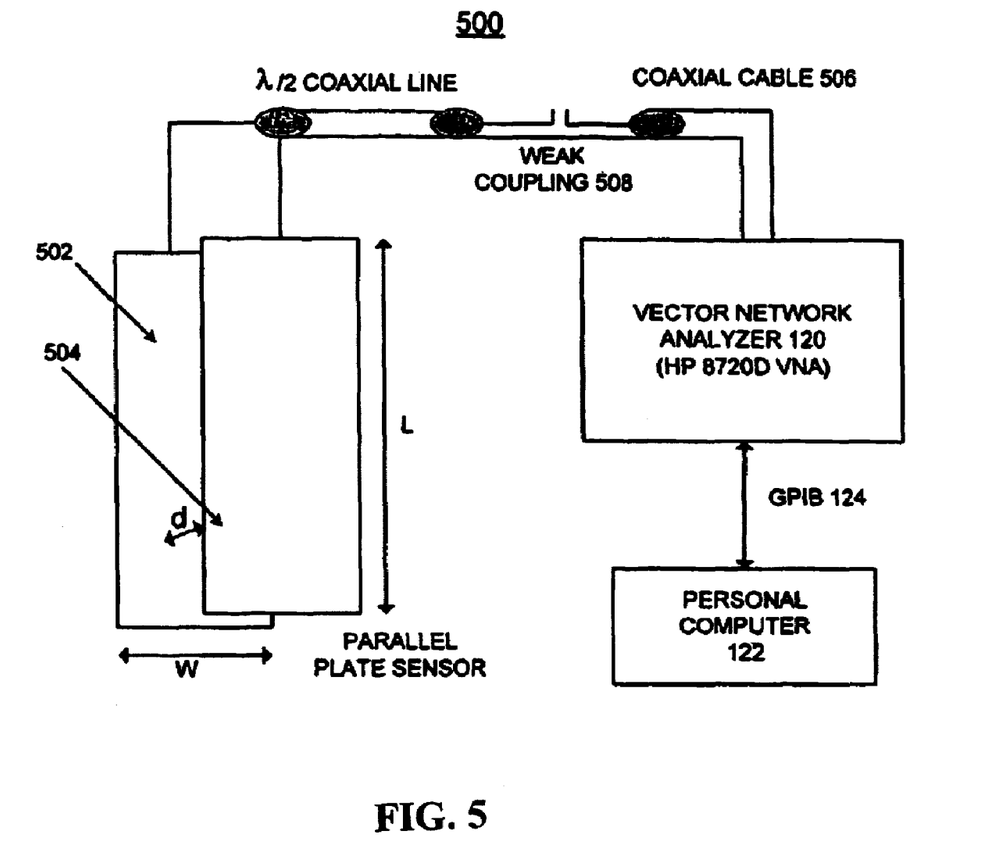
FIG. 5 is a schematic diagram illustrating an exemplary parallel plate resonator, resonator coupling mechanism, and the measurement setup for implementing dielectric sensing methods in accordance with the preferred embodiment.

Referring now to FIG. 5, there is shown an exemplary parallel plate resonator generally designated by reference character 500 for implementing dielectric sensing methods in accordance with the preferred embodiment. Parallel plate resonator 500 as shown in FIG. 5 was built and tested for soil contaminant measurements. Because the soil is generally lossy, the resonator 500 was built at RF frequencies (50 to 1000 MHz) to enable adequate depth of penetration in the soil. Parallel plate resonator 500 includes a pair of parallel plates 502, 504 that serve as a half-wavelength, or multiples of half-wavelength, open resonator. The parallel plates 502, 504 are simple, inexpensive, and can last for a long time in the soil environment with a suitable protective coating. The characteristic impedance, $Z_0$, of a parallel-plate transmission line is given by:

$$Z_0 = \frac{377d}{w\sqrt{\varepsilon_r'}} \quad (7)$$

where d is the plate separation and w the width of the plates 502, 504. The width w=2 in. and plate separation d=0.25 in. was selected to provide a characteristic impedance of 50 Ω. A 6 in. long (height of the plates indicated by arrow L) open resonator 500 was connected to a 5.5 in. long coaxial cable 506. A weak coupling 508 was used to excite the resonator 500. Reflection coefficient ($S_{11}$) measurements were made using the same HP 8720D vector network analyzer 120 and data processing using computer 122 as shown in FIG. 1.

Topsoil was placed in a conventional oven and dried. A fixed amount of the topsoil, 447 g, was then placed into a plastic container. The parallel plate sensor plates 502, 504 were then inserted three inches into the topsoil by a computer-controlled translation stage (not shown). Various chemicals were injected between the plates by means of a syringe at 0.5 cc increments from 0.5 to 4.5 cc. Data were collected at each concentration after a one minute interval to allow for the chemical to migrate through the soil. Four chemicals were tested including isopropanol, acetone, methanol, and ethanol.

Figure 6:
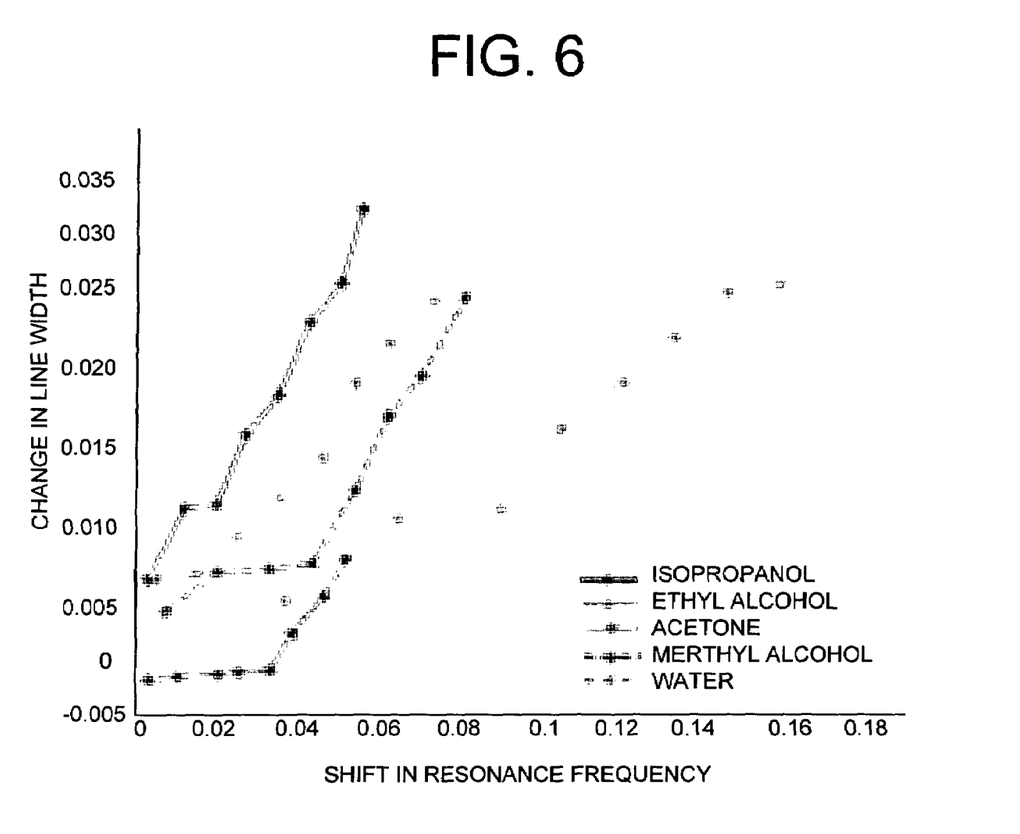
FIG. 6 is a chart illustrating a typical resonance response of the parallel plate resonator of FIG. 5 for a plurality of liquid contaminants in a dry soil sample.

FIG. 6 provides the δT-δF resonance curves for the various amounts of chemicals infiltrated in the soil sample. A moderate level of chemical selectivity is exhibited; for example, chemicals with low loss and high permittivity lie closer to the abscissa and those with high loss and low permittivity lie close to the ordinate.

In brief summary, a new dielectric sensing technique has been provided for detection and identification of chemical and biological materials in gas, liquid, or solid form. The microwave cavity resonator 100 of FIG. 1 was tested for gas and solids samples, and the RF parallel-plate resonator 500 was tested for subsurface liquid contaminant detection. Compared to conventional dielectric methods that lack selectivity to identify materials, the new technique offers a modicum of selectivity at any resonance frequency suitable for the sample under test. If the resonance frequency, however, is selected to match the dielectric relaxation or spectroscopic resonance of the sample material, the selectivity can be significantly improved. The resonance technique, because of its high quality factor, offers higher detection sensitivities than non-resonant techniques.

While the present invention has been described with reference to the details of the embodiments of the invention shown in the drawing, these details are not intended to limit the scope of the invention as claimed in the appended claims.

What is claimed is:

1. A dielectric sensing method for detection and classification of chemical and biological materials comprising the steps of:
providing a resonator for receiving a sample;
providing a sequence of reference samples having varying concentration of chemical and biological materials;
detecting generated resonance patterns of said sequence of reference samples;
identifying a shift in resonance frequency and a change of line width from said generated resonance patterns;
using said identified shift in resonance frequency and said change of line width for determining a complex dielectric constant of the sample for the material detection and classification of the sample; and
using said generated resonance patterns for real-time identifying chemical and biological materials of the sample.

2. A dielectric sensing method for detection and classification of chemical and biological materials as recited in claim 1 further includes generating said resonance patterns as a function of excitation frequency for a given sample and wherein the step of providing said resonator for receiving said sample includes the step of providing a microwave cavity resonator for receiving gas and solids samples; said cylindrical microwave cavity resonator having a cavity adjusting mechanism for adjusting a height of said cylindrical microwave cavity resonator.

3. A dielectric sensing method for detection and classification of chemical and biological materials as recited in claim 2 further includes providing a gas inlet and a gas outlet in an end plate of said microwave cavity resonator for receiving gas samples.

4. A dielectric sensing method for detection and classification of chemical and biological materials as recited in claim 2 further includes providing a sample holder on an end plate of said microwave cavity resonator located at a selected location for maximum magnetic field.

5. A dielectric sensing method for detection and classification of chemical and biological materials as recited in claim 1 wherein the step of providing said resonator for receiving said sample includes the step of providing a parallel plate resonator for receiving liquid samples for soil contaminant measurement.

6. A dielectric sensing method for detection and classification of chemical and biological materials as recited in claim 5 includes arranging said parallel plate resonator for RF frequencies in a range between 50 to 1000 MHz.

7. A dielectric sensing method for detection and classification of chemical and biological materials as recited in claim 1 wherein the steps of detecting resonance patterns and identifying said shift in resonance frequency and said change of line width before and after introduction of the sample into said resonator includes the step of selecting an excitation frequency corresponding to a resonance frequency of the sample material under test.

8. A dielectric sensing method for detection and classification of chemical and biological materials as recited in claim 1 wherein the steps of detecting resonance patterns and identifying said shift in resonance frequency and said change of line width before and after introduction of the sample into said resonator includes the step of selecting a microwave excitation frequency for detecting resonance patterns.

9. A dielectric sensing method for detection and classification of chemical and biological materials as recited in claim 8 wherein said shift in resonance frequency is represented by $\delta F=(f_o-f_s)/f_s$ where $f_o$ and $f_s$ are the resonant frequencies before and after introduction of the sample into said resonator.

10. A dielectric sensing method for detection and classification of chemical and biological materials as recited in claim 8 wherein said change in line width is represented by
$\delta T=((1/Q_{Us})-(1/Q_{U0}))$, where $Q_{U0}$ and $Q_{Us}$ represent unloaded quality factors before and after introduction of the sample into said resonator.

11. A dielectric sensing method for detection and classification of chemical and biological materials as recited in claim 1 wherein the steps of detecting resonance patterns and identifying said shift in resonance frequency and said change of line width before and after introduction of the sample into said resonator includes the step of selecting an RF excitation frequency for detecting said resonance patterns.

12. A dielectric sensing method for detection and classification of chemical and biological materials as recited in claim 1 wherein the steps of providing a sequence of resonance samples having varying concentrations of chemical and biological materials includes selectively varying sample vapor concentrations by varying a flow rate of a carrier gas for a plurality of tests.

13. A dielectric sensing method for detection and classification of chemical and biological materials as recited in claim 1 wherein the steps of providing a sequence of resonance samples having varying concentrations of chemical and biological materials includes selectively varying sample vapor concentrations by varying a vapor pressure of a liquid under test for a plurality of tests.

14. A dielectric sensing method for detection and classification of chemical and biological materials as recited in claim 1 wherein the steps of providing a sequence of resonance samples having varying concetrations of chemical and biological materials includes selectively varying sample vapor concentrations by varying a flow rate of a carrier gas and varying a vapor pressure of a liquid under test for a plurality of tests.

15. A dielectric sensing method for detection and classification of chemical and biological materials as recited in claim 1 wherein the steps of providing a sequence of resonance samples having varying concentrations of chemical and biological materials includes selectively varying sample concentrations by varying a percent by volume sample dilution for a plurality of tests.

* * * * *